US00PP21404P2

(12) United States Plant Patent
Houbraken

(10) Patent No.: US PP21,404 P2
(45) Date of Patent: Oct. 19, 2010

(54) ***OSTEOSPERMUM* PLANT NAMED 'OSECSPOVAN'**

(50) Latin Name: *Osteospermum ecklonis*
Varietal Denomination: Osecspovan

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 367 days.

(21) Appl. No.: 11/582,238

(22) Filed: Oct. 17, 2006

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
(74) *Attorney, Agent, or Firm*—S. Matthew Edwards

(57) ABSTRACT

A new *Osteospermum* plant particularly distinguished by its compact rounded plant habit, intense vanilla color and stable spoon flowering character.

1 Drawing Sheet

Latin name of genus and species of the plant claimed: *Osteospermum ecklonis*.

Varietal denomination: 'Osecspovan'.

BACKGROUND OF THE NEW PLANT

The present invention relates to a new and distinct cultivar of *Osteospermum* plant, botanically known as *Osteospermum ecklonis*.

The new *Osteospermum* is propagated by cuttings resulting from an open pollinated population from a proprietary *Osteospermum ecklonis* seedling selection as the female, or seed, parent identified as breeder's code 'D0434-1' (unpatented). Breeder's code of new plant is 'G0145-5'.

The new *Osteospermum* was discovered and selected as a single flowering plant within the progeny of the stated population grown in Enkhuizen, Netherlands, in 2002. The new *Osteospermum* plant has been repeatably asexually reproduced by cuttings in Enkhuizen, Netherlands over a period of 4 years. The new variety is stable and reproduces true to type in successive generations of asexual reproduction.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Osteospermum* plant The data which defines these characteristics were collected from asexual reproductions carried out in Enkhuizen, Netherlands. The plant history was taken on 28 week old plants. The instant plant was grown indoors in a 10.5 cm container and transplanted into the open field in week 20.

Plants of the cultivar 'Osecspovan' have not been observed under all possible environmental conditions. The phenotype may vary somewhat with variations in environment such as temperature, light intensity, day length, and fertility level without, however, any variance in genotype .

Color references are primarily to The R.H.S. Colour Chart of The Royal Horticultural Society of London, edition 2001.

Plants of the new *Osteospermum* differ primarily from the plants of the female parent 'D0434-1' in the following characteristics:

Plants of the new *Osteospermum* have a more compact plant habit, are better branching, and are more floriferous throughout the summer than plants of the female parent 'D0434-1'.

TABLE 1

DIFFERENCES BETWEEN THE NEW CULTIVAR 'OSECSPOVAN' AND A SIMILAR CULTIVAR

| | 'Osecspovan' | 'Cape Daisy Nasinga white' (unpatented) |
|---|---|---|
| Flower color | 146A | 155D |
| Rolled petals | 8D | 7D |
| Plant width | 45 cm | 50 cm |
| Flower size | 4.5-5 cm | 4.5-5.5 cm |

The plant:

*Classification.*—Botanical: *Osteospermum ecklonis.*

Parentage:

*Female parent.*—Proprietary seedling selection 'D0434-1'.

*Male parent.*—Female is open pollinated so male is unknown.

Plant description:

*Growth habit.*—Round, compact.

*Plant height.*—30 cm.

*Speading area of plant.*—45 cm.

*Strength.*—Moderate growth.

*Branching character.*—Freely branching, 18 lateral branches without pinching.

*Blooming period.*—From May until October.

The stem:

*Length.*—25 cm.

*Diameter.*—4 mm.

*Internode length.*—5-25 mm.

*Texture.*—Glabrous.

*Color.*—RHS 144A.

The foliage:

*Shape.*—Single leaves, alternate and elliptic, apex: broadly acute base: attenuate, margin: irregular serration.

*Number of leaves per lateral branch.*—70.

*Texture.*—Glabrous, leathery.

*Leaf.*—-Color-Upper side: RHS 137A. Color-Under side: RHS 137B. Length: Young 20-30 mm, mature 70-90 mm. Width: Young 4-6 mm, mature 20-23 mm.

*Petiole.*—Absent.

The inflorescence:

*Number of inflorescences per mature plant.*—40.

*Inflorescence bud.*—Form: Ovoid. Length: 10-12 mm. Width: 6-10 mm. Color: RHS 151C.

*Inflorescence lastingness on the plant.*—Around 5 days depending on the temperature.

*Inflorescence.*—Diameter: 45-50 mm. Disc diameter: 9 mm. Inflorescence depth: 8 mm.

*Fragrance: No fragrance.*

*Disc florets.*—Shape Tubular, elongated. Apex: Five pointed. Length: 8 mm. Width: 1 mm. Number of disc florets per inflorescence: 55. Color: RHS 156A.

*Ray florets*—Length: 22 mm. Width Base: 3 mm. Middle between base and apex: 1.5 mm. Apex: 4 mm. Shape: Capitulum with one series of ray florets. Color Upper surface Apex: RHS 155A. Base: RHS 155D. Lower surface Apex: RHS 8C. Base: RHS 8D. Rolled petals: 8D. Number of ray florets: 17-19. Shape: Spatulate. Apex: Rounded. Base: Acute. Margin: Entire. Texture: Satiny.

*Peduncles.*—Length: 5-8 cm. Texture: Sturdy, tiny hairs. Color: RHS 144A. Diameter: 2 mm. Shape: Round.

*Phyllaries.*—Texture: Rough, tiny hairs. Number of phyllaries.—14-16. Color: RHS 146A. Length: 10 mm. Margin: Entire. Width: 1 mm. Apex: Acute. Shape: Ligulate. Color: RHS 146B both sides.

Reproductive organs:

*Androecium.*—Appearance: Present on disc florets only. Shape: Oblong, five stamens fused to one. Length: 2 mm. Width: 1 mm. Pollen color: RHS 23A. Total no. of anthers: 60.

*Gynoecium.*—Appearance: Present on both ray and disc florets. Pistil number: One pistil per ray or disc floret. Pistil length: 4 mm. Stigma color: RHS 22A. Stigma shape: Bipartite. Style color: 160C.

Seed development: Seed development has been observed on plants of the new *Osteospermum.*

*Amount of seeds produced.*—Moderate.

*Seed length.*—5 mm.

*Diameter.*—3 mm.

*Color.*—RHS 200A.

*Shape.*—Elliptic.

Disease resistance: Under commercial conditions, plants of the new *Osteospermum* are resistant to fungal pathogens common to *Osteospermum.*

What is claimed is:

1. A new and distinct variety of *Osteospermum* plant, substantially as illustrated and described herein.

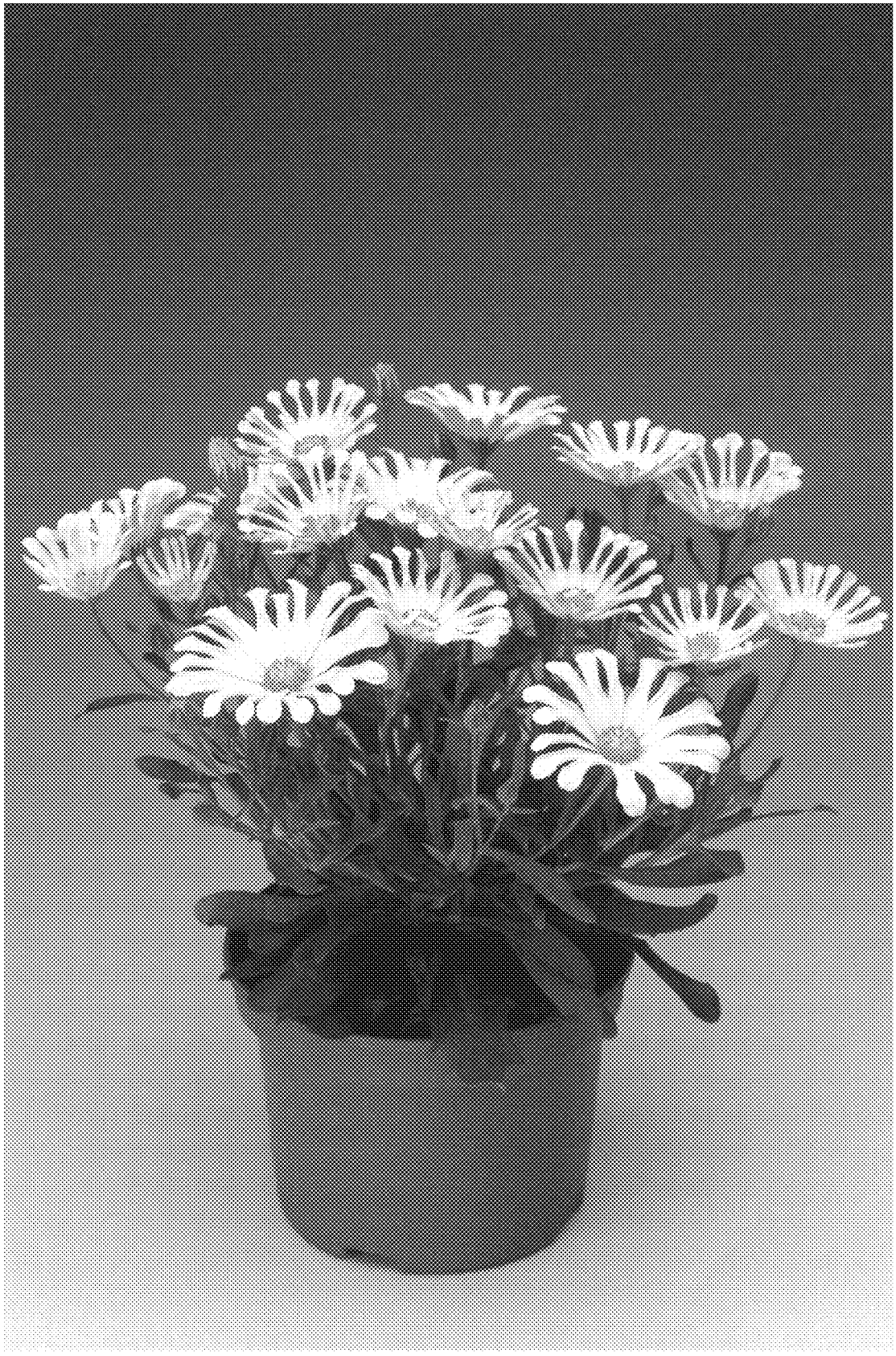

* * * * *